United States Patent
Di Lorenzo et al.

(10) Patent No.: US 7,805,773 B2
(45) Date of Patent: Oct. 5, 2010

(54) SURGICAL GLOVE

(76) Inventors: Joseph Di Lorenzo, 44 Hilltop Dr., Laurel Hollow, NY (US) 11791; Matthew Di Lorenzo, 44 Hilltop Dr., Laurel Hollow, NY (US) 11791

( * ) Notice: Subject to any disclaimer, the term of this patent is extended or adjusted under 35 U.S.C. 154(b) by 632 days.

(21) Appl. No.: 11/716,796

(22) Filed: Mar. 12, 2007

(65) Prior Publication Data

US 2008/0222774 A1 Sep. 18, 2008

(51) Int. Cl.
*A41D 19/00* (2006.01)

(52) U.S. Cl. .......................................... 2/168

(58) Field of Classification Search ............... 2/164, 2/168
See application file for complete search history.

(56) References Cited

U.S. PATENT DOCUMENTS

| | | | |
|---|---|---|---|
| 2,170,722 A * | 8/1939 | Mainzer | ...................... 70/179 |
| 3,411,982 A | 11/1968 | Kavalir | |
| 4,061,709 A | 12/1977 | Miller | |
| 4,302,852 A | 12/1981 | Joung | |
| 4,310,928 A | 1/1982 | Joung | |
| 4,430,759 A * | 2/1984 | Jackrel | ........................... 2/159 |
| 4,696,065 A | 9/1987 | Elenteny | |
| 4,748,693 A * | 6/1988 | Shinn | ............................. 2/164 |
| 4,947,486 A * | 8/1990 | Hsuih | ............................. 2/164 |
| 5,357,636 A | 10/1994 | Dresdner, Jr. | |
| 5,568,656 A | 10/1996 | Kim | |
| 5,741,885 A * | 4/1998 | Dove | ......................... 604/349 |
| 5,907,870 A | 6/1999 | Monroe et al. | |
| 5,993,923 A | 11/1999 | Lee | |
| 6,016,570 A | 1/2000 | Vande Pol | |
| 6,154,886 A | 12/2000 | Hottner | |
| 6,415,446 B1 * | 7/2002 | McLean et al. | ............... 2/161.6 |
| 6,543,059 B2 * | 4/2003 | Szczesuil et al. | ............. 2/161.6 |
| 6,594,830 B2 | 7/2003 | Geng | |
| 6,596,345 B2 | 7/2003 | Szczesuil | |
| 6,918,241 B2 | 7/2005 | Zhu | |
| 6,979,734 B1 | 12/2005 | Paping | |
| 2003/0066120 A1 | 4/2003 | Tremblay-Lutter | |
| 2005/0268374 A1 | 12/2005 | Mattesky | |
| 2006/0010565 A1 | 1/2006 | Teoh | |

* cited by examiner

*Primary Examiner*—Katherine Moran
(74) *Attorney, Agent, or Firm*—Stetina Brunda Garred & Brucker

(57) ABSTRACT

There is provided a glove assembly that is adapted to be worn on a human hand for use in extended medical procedures such as surgery. The assembly may include an inner glove of permeable polyester fabric. There may additionally be a coating adhered to the inner glove, which prevents seepage of fluid through the inner glove from an internal surface to an external surface thereof. The assembly may further include an outer glove with interior dimensions substantially equivalent to the exterior dimensions of the inner glove. The outer glove may be in a receiving relationship to the inner glove.

14 Claims, 3 Drawing Sheets

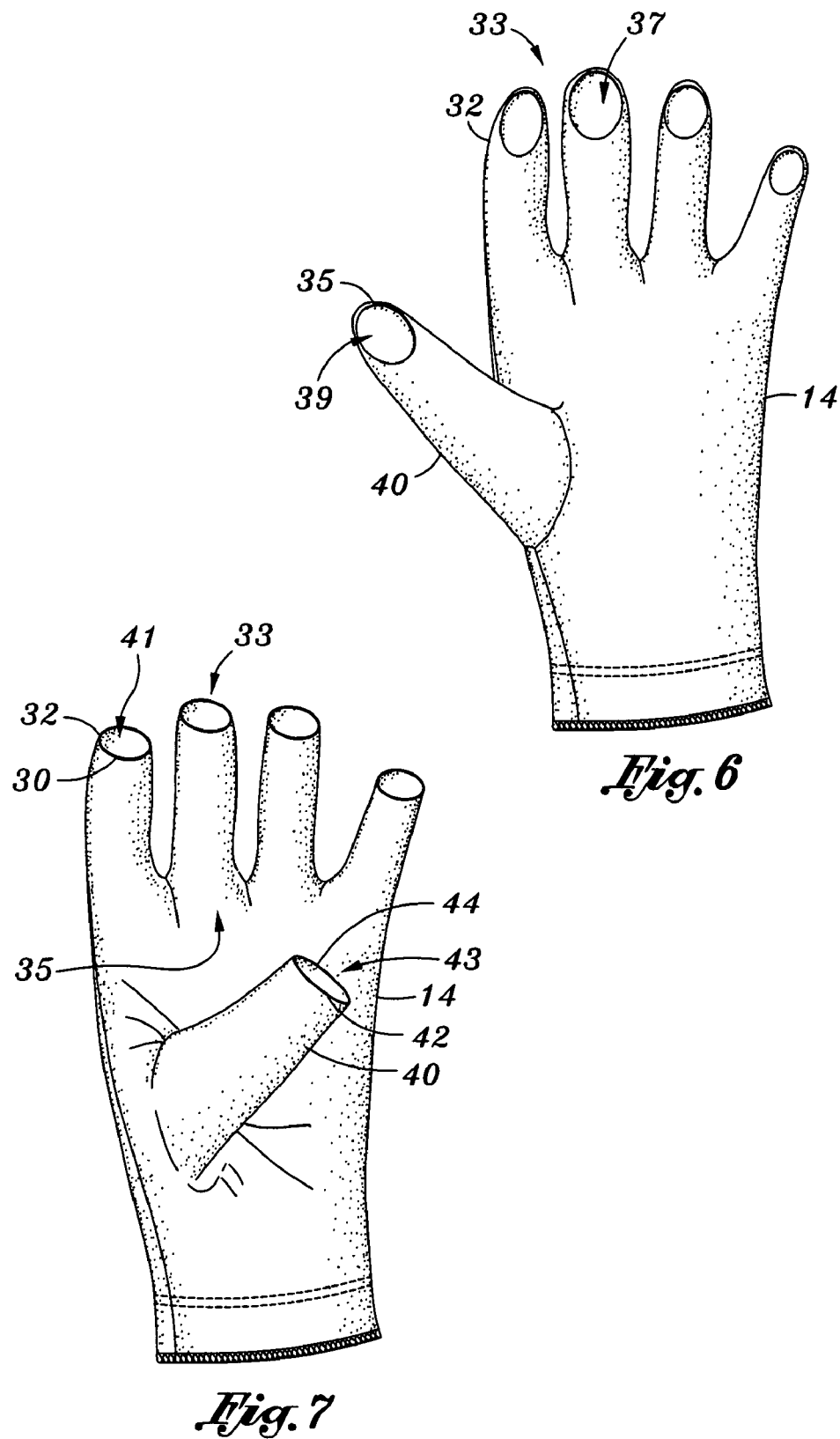

SURGICAL GLOVE

CROSS-REFERENCE TO RELATED APPLICATIONS

Not Applicable

STATEMENT RE: FEDERALLY SPONSORED RESEARCH/DEVELOPMENT

Not Applicable

BACKGROUND

1. Technical Field

The present invention generally relates to protective wearing apparel. More particularly, the present invention relates to gloves with improved tactile feel and comfort for extended use in medical related procedures and facilities.

2. Related Art

Gloves are universally utilized in surgical procedures to reduce the transmission of contaminants to a patient, as well as to reduce the transmission of the patient's bodily fluids to the surgeon and support personnel. While this functionality is an important consideration in the development of surgical gloves, of equal importance is the comfort and retention of tactile sensitivity to the wearer. Surgical procedures may last for extended periods of time, and so it is important for the glove to remain comfortable throughout a substantial portion of the surgery until such time that it may be replaced, if not for the entirety of the surgery. Due to the extended period of wear under stressful conditions, perspiration and the pooling thereof inside the glove increases discomfort. Additionally, excess perspiration may cause slippage between the hand and the glove wall, thereby exposing the patient, the surgeon, and other personnel to significant risk of harm.

Earlier surgical gloves were constructed of natural latex, but due to allergic reactions in some patients, as well as surgeons, conventional gloves are of the synthetic latex variety. Additionally, surgical gloves made of rubber cement, and silicone rubber, have also been developed. As contemplated in U.S. Pat. No. 3,411,982 to Kavalir, et al., latex gloves are typically formed by dipping or otherwise depositing an appropriately configured hand-shaped form into a coagulant and latex bath. The latex may contain a vulcanizing agent such as sulfur, along with accelerators and preservatives. After dipping, the latex is cured and dried, yielding a completed glove.

Since there is a tendency for the glove to stick to the mold after curing, a powder lubricant may be included in the coagulant dip, or otherwise applied to the glove. The powder lubricant is usually talc because it can withstand curing temperatures. However, gloves manufactured with a coagulant containing such talc powders were problematic in that the talc powders have a tendency to create granuloma upon contact with a surgical wound. Additionally, the talc can leave a residue on equipment and clothing, and interfere with surgical procedures. Despite efforts to wash the talc off after curing, the particles were embedded fully or partially into the glove wall, making it difficult to remove. In response to this deficiency, U.S. Pat No. 4,302,852 to Joung proposes gloves manufactured without a powdered lubricant incorporated into the coagulant. Instead of talc powder, the '852 disclosure contemplates a silicone coating applied to the interior of the glove after dipping the glove in the latex bath. As understood, this eases the difficulty of removing the glove from the form after curing, while not entirely eliminating the need for a donning powder.

As briefly indicated above, it may be necessary for the surgeon to remove a pair of surgical gloves after a certain period of time due to the accumulation of perspiration within the interior, tears on the surface, accumulation of blood and other bodily fluids of the patient on the exterior, and so forth. Thus, another important characteristic of latex gloves is its ease of donning, that is, the ability to be slid over the skin surface of the wearer's hand. The friction encountered in donning surgical gloves should be reduced with respect to wet skin as well as dry skin. In this regard, the talc powder incorporated into the coagulant also serves as a donning powder or lubricant.

With the elimination of lubricant powder in the production of surgical gloves, alternative friction reduction means became necessary. Other types of lubricants such as silicone oil, fatty acids, surfactants, and the like may be applied to the interior of the glove prior to donning. However, these gel and liquid lubricants exhibit the same problems as powder lubricants.

An alternative surgical glove that eliminates the problematic lubricating powder is disclosed in U.S. Pat. No. 5,993,923 to Lee. The Lee disclosure contemplates a rubber glove with a coating deposited on its surface that is an elastic, powder-free, non-tacky, emulsion acrylic copolymer. It is understood that the coating enhanced the donning characteristics of the glove, while maintaining tactile feel as well as resiliency for the preventing tear.

Considering the non-breathable nature of latex, however, after prolonged periods of wear, all latex gloves are limited in that perspiration begins to collect within. Therefore, there is a need in the art for a surgical glove having enhanced tactile feel and improved donning characteristics, while also preventing the pooling of perspiration that may result in slippage. Furthermore, there is a need in the art for a surgical glove assembly with an inner layer capable of wicking away perspiration, and a resilient outer layer.

BRIEF SUMMARY

In accordance with one embodiment of the present invention, there is provided a glove assembly adapted to be worn on a human hand for use in extended medical procedures. The glove assembly may include an inner glove of permeable polyester fabric having moisture wicking characteristics. The inner glove may define an internal surface and an external surface. In another aspect, there may be a substantially non-porous coating adhered to the external surface of the inner glove. The coating may penetrate the inner glove to a depth short of the internal surface of the inner glove, thereby preventing seepage of fluid through the inner glove from the internal surface to the external surface. In one embodiment of the present invention, the coating is latex. The glove assembly may also include an outer glove with interior dimensions substantially equivalent to the exterior dimensions of the inner glove. The outer glove may be in a receiving relationship to the inner glove. Preferably, the outer glove is formed of synthetic latex and is powder-free.

In another aspect of the present invention, the inner glove may be defined by a ventral segment and a dorsal segment stitched together partially along the peripheral edges thereof. The stitching between the ventral segment and the dorsal segment may be unexposed to the external surface of the inner glove. The ventral segment and the dorsal segment may each include finger portions which may define openings. The finger portions on the ventral segment may be symmetrical to the finger portions of the dorsal segment. The inner glove may also include a thumb portion extending from an opening on the ventral segment of the inner glove. In some embodiments, the thumb portion may define an opening. The thumb portion may be stitched to the ventral segment. The stitching between the ventral segment and the thumb segment may be unexposed to the outer external surface of the inner glove. The thumb portion may also be defined by a ventral thumb segment and a dorsal thumb segment partially stitched together along the peripheral edges thereof.

According to one embodiment of the present invention, the substantially non-porous coating is adhered only to the ventral thumb segment and the ventral segment of the inner glove.

The present invention will be best understood by reference to the following detailed description when read in conjunction with the accompanying drawings.

BRIEF DESCRIPTION OF THE DRAWINGS

These and other features and advantages of the various embodiments disclosed herein will be better understood with respect to the following description and drawings, in which like numbers refer to like parts throughout, and in which:

FIG. 6 is a perspective view of the inner glove according to another embodiment, with the ventral segment of the finger portions defining an opening;

FIG. 7 is a perspective view of the inner glove according to yet another embodiment, where the ventral and dorsal segments of the finger portions collectively define an opening.

Common reference numerals are used throughout the drawings and the detailed description to indicate the same elements.

DETAILED DESCRIPTION

The detailed description set forth below in connection with the appended drawings is intended as a description of the presently preferred embodiment of the invention, and is not intended to represent the only form in which the present invention may be constructed or utilized. It is understood that the use of relational terms such as first and second, top and bottom, and the like are used solely to distinguish one from another entity without necessarily requiring or implying any actual such relationship or order between such entities.

Figure 1:
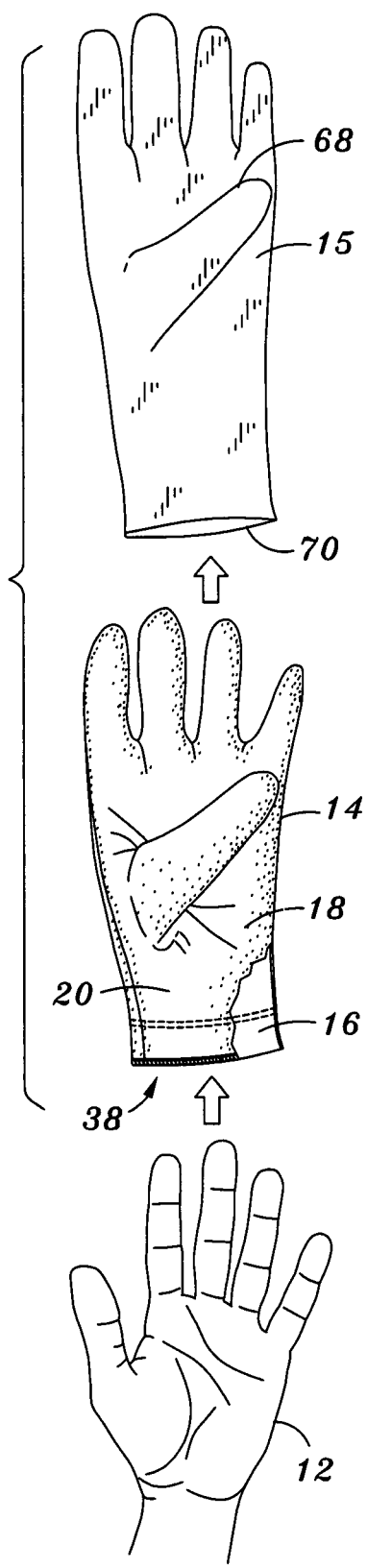
FIG. 1 is a diagrammatic illustration of a glove assembly for use with a human hand, in accordance with one aspect of the present invention.

With reference to FIG. 1, the glove assembly 10 according to an embodiment of the present invention is illustrated, with a human hand 12 being inserted therein. The glove assembly 10 is adapted to be worn on the human hand 12 for use in extended medical procedures such as surgery. While the exemplary glove assembly 10 is illustrated with the left hand and accommodating the same, it will be understood by those having ordinary skill in the art that the inventive features of the present invention are equally applicable to a glove assembly that can accommodate a right hand. It will be further understood that the glove assembly 10 may be sized to accommodate a wide range of hand sizes and types. As is conventionally practiced, the glove assembly 10 may have stepwise increases in length, width, and other hand geometries. In a preferred embodiment, the glove assembly 10 is sized to closely fit the hand 12 without being overly restrictive to enhance tactile sensitivity.

The glove assembly 10 includes an inner glove 14 of a polyester fabric having moisture wicking features, and defines an internal surface 16 and an external surface 18. As is well known, a fabric comprised of pure polyester is characterized by low absorbency, and so may be blended with other fabrics to increase absorbency. Alternatively, the strands of polyester fiber may be woven together to define channels that allow air to flow through the fabric. These channels also draw moisture to the surface of the fabric, thereby keeping the level of moisture within the glove to a minimum. One well known fabric exhibiting these characteristics is sold under the trade name COOLMAX by E. I. du Pont de Nemours and Company of Wilmington, Del. It is expressly contemplated that other like performance or conventional fabrics exhibiting such wicking characteristics may be readily substituted without departing from the scope of the present invention. For example, a substitute fabric may be sold under the trade name THERMASTAT, THERMAX, or TACTEL, each from E. I. du Pont de Nemours and Company. In order to maintain tactile sensitivity with respect to the inner glove 14, the weight and thickness of the fabric is to be minimized.

Figure 2:
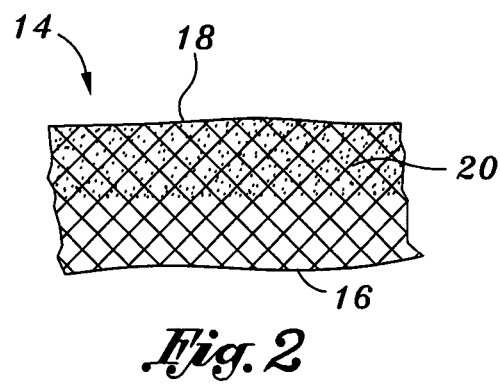
FIG. 2 is a cross-sectional view of an inner glove, with a coating adhered thereto to a depth short of its internal surface.

With reference to FIG. 2, which is a cross-sectional view of the sheet of fabric comprising the inner glove 14, and with additional reference back to FIG. 1, there is a substantially non-porous coating 20 adhered to the external surface 18 of the inner glove 14. The coating 20 penetrates to a depth short of the internal surface 16. Thus, the coating 20 limits the seepage of perspiration from the internal surface 16 to the external surface 18. According to a preferred embodiment of the present invention, the coating 20 is a latex compound, although any suitable substantially non-pours material may be readily substituted. The coating 20 may be applied to the inner glove 14 by dipping, spraying, or any other suitable method.

Figure 3:
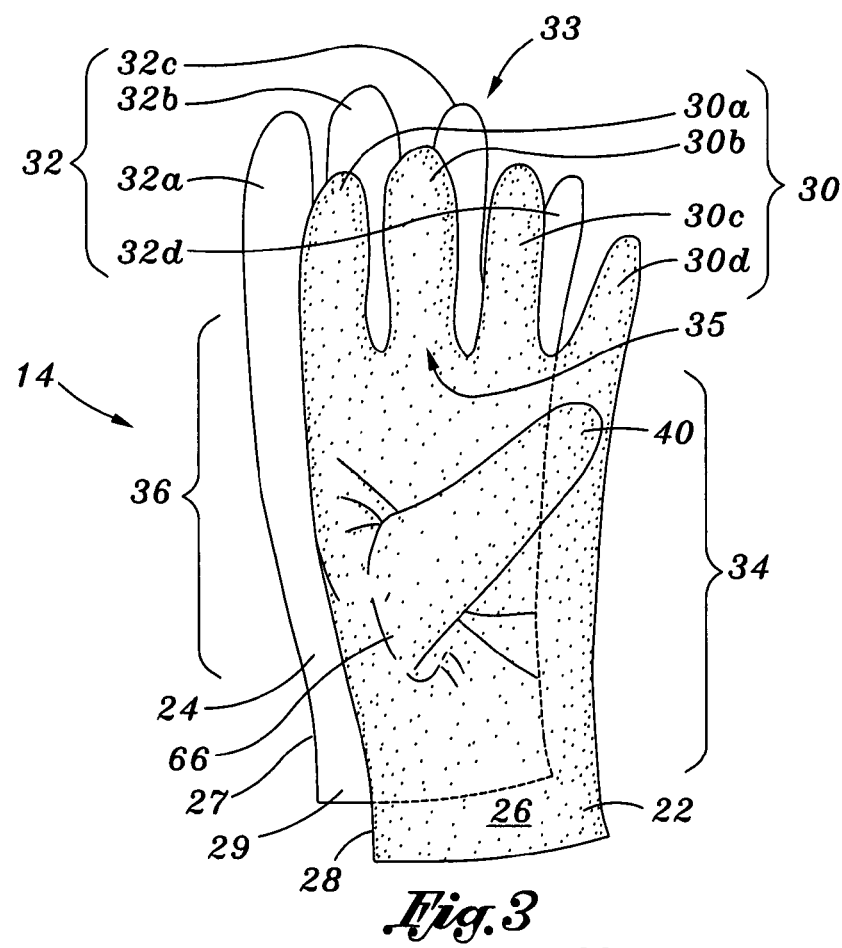
FIG. 3 is a perspective view of the inner glove in accordance with an aspect of the present invention, with a ventral segment and a dorsal segment thereof being separated.

Referring now to FIG. 3, the inner glove 14 is defined by a ventral segment 22 and a dorsal segment 24, which are pieces of the fabric thereof. The ventral segment 22 is defined by an external ventral segment surface 26 and an internal ventral segment surface 28. The dorsal segment 24 is defined by an external dorsal segment surface 27, and an internal dorsal segment surface 29. Both the ventral segment 22 and the dorsal segment 24 may be further segregated into finger portions 30 and 32, respectively, and palm portions 34 and 36, respectively. More specifically, the finger portion 30 is comprised of an index finger 30a, a middle finger 30b, a ring finger 30c, and a little finger 30d. The finger portion 32 is likewise comprised of an index finger 32a, a middle finger 32b, a ring finger 32c, and a little finger 32d. The finger portions 30, 32 each define a distal end 33, and a proximal end 35 connected with the palm portions 34, 36. It is understood that the finger portion 30 of the ventral segment 22 is symmetrical to the finger portion 32 of the dorsal segment 24.

Figure 4A:
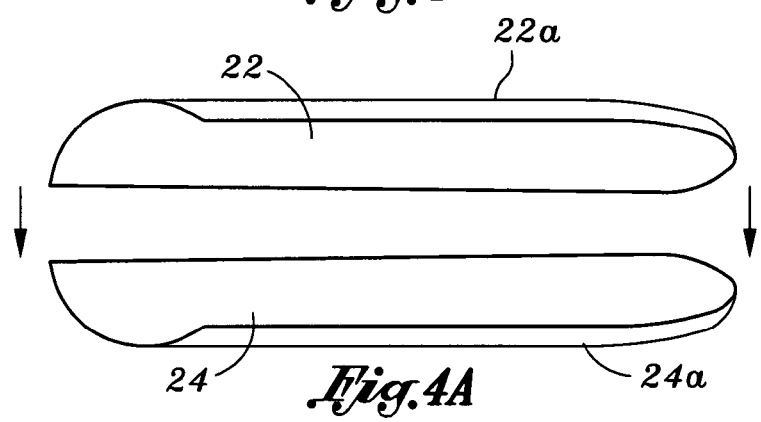
FIG. 4a is a perspective view of a finger portion of the inner glove separated into the ventral segment and the dorsal segment.
Figure 4B:
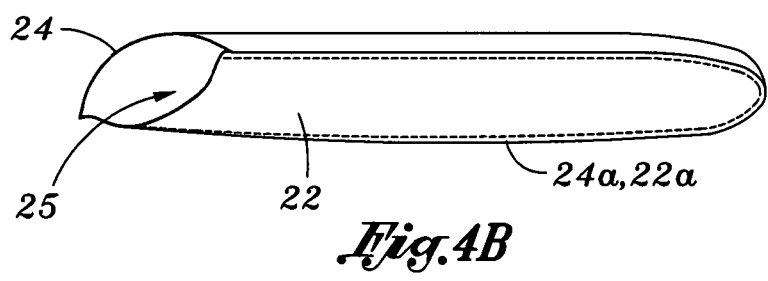
FIG. 4b is a perspective view of the finger portion of the inner glove with peripheral edges of the ventral and dorsal segments being stitched together in accordance with an aspect of the present invention.

As partially illustrated in FIG. 4, the ventral segment 22 and the dorsal segment 24 are stitched together along the peripheral edges 22a, 22b, thereof, leaving an interior compartment 25 for receiving the hand 12. While FIG. 4 illustrates the ventral segment 22 and the dorsal segment 24 of the finger portions 30 and 32 being stitched together, it will be understood that other parts of the inner glove 14, namely, the palm portions 34 and 36, are similarly stitched together. However, there is an open cuff 38 for receiving the hand 12. According to a preferred embodiment of the present invention, the stitches between the ventral segment 22 and the dorsal segment 24 are formed within the inner glove 14. Alternative attachment modalities are expressly contemplated, such as the use of adhesives and fusing the two segments together via heat.

Figure 5A:
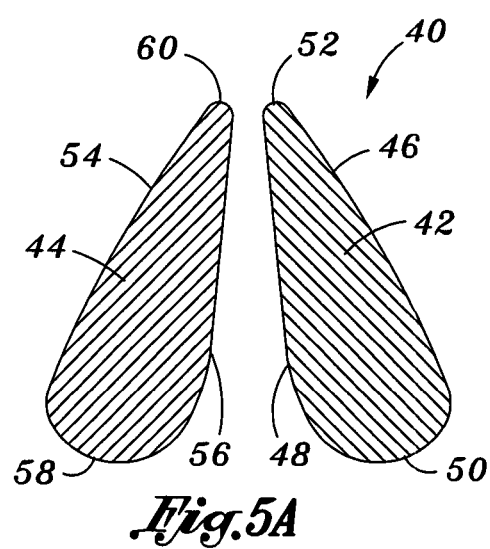
FIG. 5a is a frontal view of a thumb portion of the inner glove separated into a ventral thumb segment and a dorsal thumb segment.
Figure 5B:
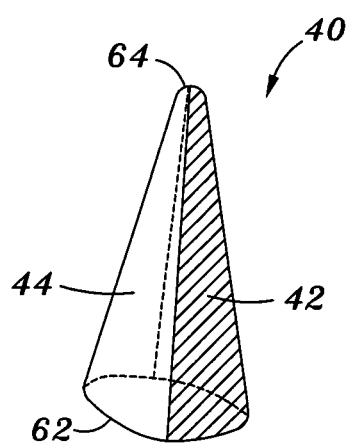
FIG. 5b is a perspective view of the thumb portion of the inner glove.

The ventral segment 22 includes a thumb portion 40 extending therefrom. Preferably, the thumb portion 40 is stitched to the ventral segment 22, and such stitching is unexposed on the external ventral segment surface 26. Referring to FIGS. 5a and 5b, the thumb portion 40 is defined by a ventral thumb segment 42 having a conical shape, including a first ventral thumb edge 46 and a second ventral thumb edge 48. The ventral thumb segment 42 is further defined by a wide base end 50 and a narrow top end 52. The thumb portion 40 is also defined by a dorsal thumb segment 44. The dorsal thumb segment 44 is, like the ventral thumb segment 42, conical in shape and defined by a first dorsal thumb edge 54, a second dorsal thumb edge 56, a wide base end 58, and a narrow top end 60. Preferably, the first ventral thumb edge 46 is attached to the first dorsal thumb edge 54, and the second ventral thumb edge 48 is attached to the second dorsal thumb edge 56, with the respective base ends 50, 58 of the ventral and dorsal thumb segments 42, 44 partially defining an open thumb cuff 62 and a closed tip 64. The ventral thumb segment 42 and the dorsal thumb segment 44 are stitched together in such a fashion that the stitches remain unexposed to prevent snags.

In accordance with another embodiment of the present invention as illustrated in FIG. 6, the distal ends 33 of the finger portions 32 define openings 37. More particularly, the ventral segment 22 of each of the finger portions 32 defines the openings 37, such that upon being donned, the fingertips are exposed, while the fingernails are covered by the dorsal segment 24. Similarly, the ventral thumb segment 42 may define an opening 39 in the vicinity of the narrow top end 52 thereof, likewise resulting in the thumb tip being exposed, while the opposing thumbnail is covered by the dorsal thumb segment 44.

In yet another alternative embodiment as shown in FIG. 7, the distal ends 33 of ventral and dorsal segments 30, 32 define openings 41. In other words, the distal ends of the finger portions 32 are truncated, such that upon donning, both the fingertips and the corresponding fingernails are exposed. This configuration may be duplicated in the thumb portion 40 as well, where the ventral thumb segment 42 and the dorsal thumb segment 44 collectively define an opening 43. As such, the thumb tip and the thumbnail may be exposed.

Referring back to FIG. 3, the palm portion 34 of the ventral segment 22 defines a thumb portion aperture 66. Preferably, the circumference of the thumb portion aperture 66 is equivalent to that of the thumb cuff 62 of the thumb portion 40. The thumb portion 40 is attached to the ventral segment 22, preferably with stitching that is unexposed on the external ventral segment surface 28. However, alternative attachment means such as heat fusing and adhesives as indicated above may be utilized as well. It will be recognized by those having ordinary skill in the art the natural position of the fingers and the thumb are better accommodated in the aforementioned geometry. In this regard, the positioning of the thumb portion 40 reduces the amount that the polyester fabric must stretch, providing increased safety and comfort.

With reference to FIG. 1, the glove assembly 10 further includes an outer glove 15 having interior dimensions substantially equivalent to the exterior dimensions of the inner glove 14. The outer glove 15 is to be donned on the inner glove 14, and maintain a tight, yet comfortable fit therewith. As understood, the outer glove 15 serves the primary function of providing a barrier between the hand 12 and the patient during surgical procedures, and is accordingly made of non-porous material. Preferably, the material is latex, although any material described in the background as being a suitable material may be readily substituted without departing from the spirit and scope of the present invention. More particularly, the material is latex manufactured without any powder lubricant in the coagulant, and without any powder added after manufacturing to improve donning characteristics. In a preferred embodiment, the outer glove is composed of material sold under the trade name BIOGEL by Mölnlycke Health Care AB of Gothenburg, Sweden. With respect to the shape and configuration of the outer glove 15, as illustrated in FIG. 1, it is similar to the shape and configuration of the inner glove 14, particularly with regard to the placement of the thumb portion 68. However, it is understood that any suitable surgical glove may be utilized instead. The outer glove 15 is typically of a unitary construction, and may include a beaded cuff 70 for securing the outer glove 15 to the surgeon's wrist.

According to the above-described configuration of the inner glove 14 and the outer glove 15, any perspiration from the hand 12 is absorbed through the fabric of the inner glove 14 and wicked away without pooling within the outer glove 15. It will be appreciated that the primary operative surface of the hand 12 is that which contacts the ventral segment 22 of and the ventral thumb segment 42 of the inner glove 14. Accordingly, moisture is more likely to accumulate in those areas of the inner glove 14, leading to pooling within the outer glove 15 in such areas that are adjacent to the ventral segment 22 and the ventral thumb segment 42 of the inner glove 14.

In one embodiment of the present invention, the ventral segment 22 has adhered to thereon the substantially non-porous coating, that is, the latex coating. As indicated above, the coating penetrates the inner glove 14 to a depth short of the internal surface 28, and so the moisture wicking capabilities of the fabric are retained, while inhibiting the escape of moisture to the external ventral segment surface 27 that may lead to pooling and slippage. While particular reference has been made to the ventral segment 22, it is understood that the same coating techniques are applicable to the thumb portion 40 and the ventral segment 42 thereof. According to the above-described embodiment, the dorsal segment 24 may not have adhered thereto the substantially non-porous coating. The moisture from the ventral segment 22 may wick towards the dorsal segment 24 and evaporate as it exits the inner glove 14 via the open cuff 38. Alternatively, the moisture may pool in the non-operative areas within the outer glove 15, that is, those areas which are adjacent to the dorsal segment 24 of the inner glove 14. As will be appreciated, pooling in this area does not appear to pose a significant slippage issue.

The particulars shown herein are by way of example and for purposes of illustrative discussion of the embodiments of the present invention only and are presented in the cause of providing what is believed to be the most useful and readily understood description of the principles and conceptual aspects of the present invention. In this regard, no attempt is made to show structural details of the present invention in more detail than is necessary for the fundamental understanding of the present invention, the description taken with the drawings making apparent to those skilled in the art how the several forms of the present invention may be embodied in practice.

What is claimed is:

1. A glove assembly adapted to be worn on a human hand for use in extended medical procedures, the glove assembly comprising:

an inner glove of permeable polyester fabric having moisture wicking characteristics, the inner glove defining an internal surface and an external surface the inner glove further having a ventral segment and a dorsal segment stitched together partially along the peripheral edges thereof, the ventral segment and dorsal segment further including integrally formed finger portions defining a distal end and a proximal palm end, the finger portions on the ventral segment being symmetrical to the finger portions of the dorsal segment;

a substantially non-porous coating adhered to the external surface of the inner glove and penetrating the inner glove to a depth short of the internal surface of the inner glove, thereby limiting seepage of fluid through the inner glove from the internal surface to the external surface; and an outer glove having interior dimensions substantially equivalent to the exterior dimensions of the inner glove, the glove being in a receiving relationship to the inner glove.

2. The glove assembly of claim 1, wherein the distal ends of the dorsal and ventral segments of the finger portions define openings.

3. The glove assembly of claim 1, wherein the distal ends of the ventral segment of the finger portions define openings.

4. The glove assembly of 1, further comprising a thumb portion extending from an opening on the ventral segment, the thumb portion being stitched to the ventral segment.

5. The glove assembly of claim 4, wherein the stitching between the ventral segment and the thumb segment is unexposed to the outer external surface of the inner glove.

6. The glove assembly of claim 4, wherein the thumb portion is defined by a ventral thumb segment and a dorsal thumb segment partially stitched together along the peripheral edges thereof, the thumb portion being further defined by a distal end and a proximal palm end.

7. The glove assembly of claim 6, wherein the ventral thumb segment and the dorsal thumb segment define a thumb tip opening.

8. The glove assembly of claim 6, wherein the ventral thumb segment defines a thumb tip opening.

9. The glove assembly of claim 6, wherein the substantially non-porous coating is adhered only to the ventral thumb segment.

10. The glove assembly of claim 1, wherein the substantially non-porous coating is adhered only to the ventral segment of the inner glove.

11. The glove assembly of claim 1, wherein the stitching between the ventral segment and the dorsal segment is unexposed to the external surface of the inner glove.

12. The glove assembly of claim 1, wherein the substantially non-porous coating is latex.

13. The glove assembly of claim 1, wherein the outer glove is formed of synthetic latex.

14. The glove assembly of claim 13, wherein the outer glove is free of powder.

* * * * *